United States Patent [19]

Cummings et al.

[11] Patent Number: 4,600,695
[45] Date of Patent: Jul. 15, 1986

[54] SODIUM FIRE SIMULATION PROCESS

[75] Inventors: Ralph L. Cummings, Anaheim Hills; Marshall L. Clark, Orange, both of Calif.

[73] Assignee: Wyle Laboratories, Norco, Calif.

[21] Appl. No.: 495,983

[22] Filed: May 19, 1983

[51] Int. Cl.[4] .............................................. G01N 17/00
[52] U.S. Cl. .................................. 436/2; 324/158 R; 422/53; 436/6
[58] Field of Search .................... 436/2, 3, 6, 39, 183; 422/53; 324/158 R, 73 R

[56] References Cited

U.S. PATENT DOCUMENTS

| | | | |
|---|---|---|---|
| 1,827,530 | 10/1931 | Le Grand | 128/1 R |
| 2,703,488 | 3/1955 | Gevantman et al. | 73/53 |
| 3,488,681 | 1/1970 | Mita et al. | 73/15.4 |
| 4,282,181 | 8/1981 | Pierce | 422/53 |

FOREIGN PATENT DOCUMENTS 1401445 7/1975 United Kingdom .

OTHER PUBLICATIONS

Effects of Low Sodium Aerosol Concentration on Electrical Equipment by-N. L. Haines, E. S. Sachse, G. R. Taylor-Westinghouse Advanced Reactors Division.

Primary Examiner—Jerry W. Myracle
Assistant Examiner—Stephen M. Baker
Attorney, Agent, or Firm—Freilich, Hornbaker, Rosen & Fernandez

[57] ABSTRACT

A method is described for testing equipment to determine whether it will continue to function when in the presence of a sodium fire, which is of much less cost than prior testing methods. The method includes spraying sodium monoxide on the equipment while it lies within an enclosure. The sodium monoxide is a fine powder, and the moisture within the chamber is maintained at a high level which is much above 20%. The moisture turns the sodium monoxide to sodium hydroxide, or lye, which is the most damaging component of a sodium fire.

5 Claims, 2 Drawing Figures

SODIUM FIRE SIMULATION PROCESS

BACKGROUND OF THE INVENTION

Sodium is an important heat transfer agent because it boils at a high temperature on the order of 1500° F. In a nuclear reactor, such as the liquid metal fast breeder reactor at Clinch River, the sodium can be used to transfer heat from the reactor core to water to create super heated steam for driving turbines. In such a reactor, the pipes carrying sodium are enclosed in a vessel in which there is also emergency equipment such as switches, motors, and valves, which must operate in the event of a sodium fire. However, if hot sodium leaks from a pipe and ignites, the products of the combustion create chemicals that are very deleterious to equipment.

In order to assure that emergency equipment will operate for long periods of time such as many weeks in the event of a sodium fire, such equipment may be subjected to a test. In a typical prior art test, equipment such as electrical relays were placed in an air-tight chamber, and cables were run through the walls of the chamber to the equipment to test operation of the equipment. Then bricks of sodium were combusted with air in a special furnace, and the gaseous products of combustion were piped into the chamber. As the piped-in products of combustion cooled, they precipitated onto the equipment as powder representing the products of combustion. The conducting of such a test can be hazardous, and results in a very high cost. A test for determining the capacity of equipment to function in the presence of the products of combustion of a sodium fire, which reduced the cost of testing, would be of considerable benefit.

SUMMARY OF THE INVENTION

In accordance with the present invention, a method is described for testing equipment to determine its capacity to continue functioning in the presence of a sodium fire, which enables such testing to be conducted at a relatively low cost. The process includes the application of an oxide of sodium, of sodium monoxide or sodium peroxide, to the equipment in a powder form, while the equipment is maintained in a sealed chamber. The humidity in the chamber is controlled so that it is at least 20%, and preferably much higher, after the powder is applied. The equipment in the chamber is then tested to determine its capacity to continue functioning properly.

The three components of a sodium fire that occur in air that contains substantial moisture, is sodium monoxide ($Na_2O$), sodium peroxide ($Na_2O_2$), and sodium hydroxide (NaOH) also known as lye. The most damaging component is the lye, particularly as it forms on the equipment when sodium monoxide and sodium peroxide combine with moisture in the air to form lye. By depositing powder of sodium monoxide and/or sodium peroxide on the equipment, and exposing the powder to an environment containing moisture, applicant subjects the equipment to the most damaging products that occur in a sodium fire. If the equipment continues to function properly, then it will function properly when exposed to the components of an actual sodium fire. The depositing of the powder on the equipment in a chamber, is much less hazardous and much less costly than the creation of an actual sodium fire and the exposing of the equipment to the gaseous products of such a fire.

Of the two sodium oxides that can be deposited, applicant prefers sodium monoxide ($Na_2O$), even though it is not readily available, because when sodium peroxide ($Na_2O_2$) is ground to a fine powder there is substantial danger of explosion.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
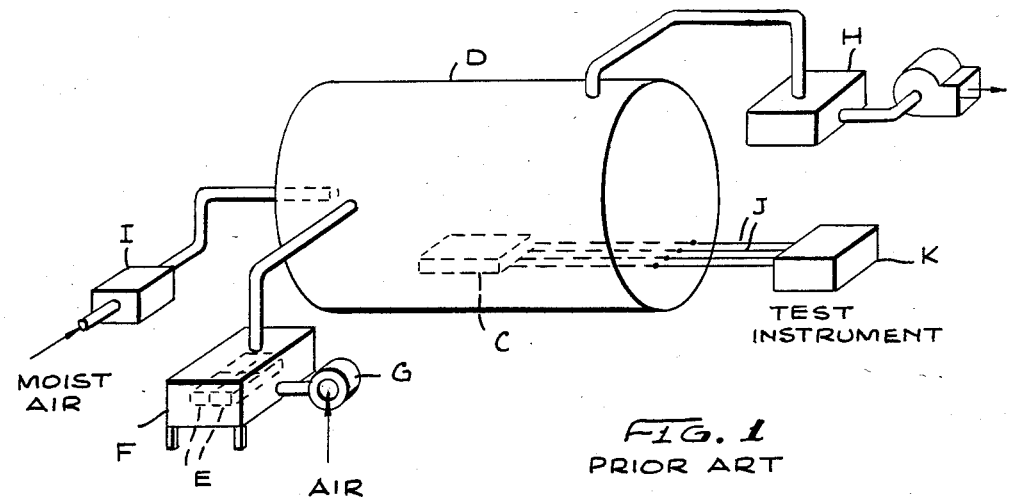
FIG. 1 is a perspective view of a prior art technique for testing equipment for its capability to function in the presence of a sodium fire.

FIG. 1 illustrates a prior art technique for testing a component C such as a relay, to determine whether or not it will function properly in the presence of a sodium fire. Such a fire can occur when there is a leak in a pipe or auxilliary equipment carrying high temperature liquid sodium or in a sodium storage vessel. The hot sodium spraying into a space containing air, will ignite, form a pool of sodium, and result in a sodium fire. The same sealed area through which the pipes carrying liquid sodium pass, also contains emergency equipment such as shutoff-valves, sensors, motors, relays, and the like which must continue to operate during an emergency such as a sodium fire to facilitate a safe shut down of the plant. The equipment is typically placed so that it will not be directly subjected to burning sodium, but is instead subjected to the products of combustion of the sodium. Such products are initially gaseous, but they then settle as a fine powder on the equipment. Since the plant may require several weeks for a shut down, the equipment must reliably operate over a period of weeks when subjected to the products of a sodium fire.

In the prior art method shown in FIG. 1, the component C was placed in a chamber D. Bricks of sodium E were burned in a combustion chamber F to which air was supplied by a blower G. The gaseous products of combustion flowed from the combustion chamber F to the equipment chamber D, and remained there for a considerable period of time. During burning of the sodium, some of the atmosphere in the chamber D was removed through a dry filter bank H to remove sodium combustion products before blowing the remaining air into the atmosphere. An accident condition may transport air of 95% humidty to the area of the sodium fire. To simulate this occurance, a temperature and humidity control unit I was also connected to the equipment-holding chamber D. During the test, cables J were run through the chamber walls to a test instruments K which tested the equipment to determine whether or not it would continue to operate within predetermined parameters.

Measurements of the products of combustion of a sodium fire, show that the three major gaseous components are sodium monoxide ($Na_2O$), sodium peroxide ($Na_2O_2$) and sodium hydroxide (NaOH). These gaseous products themselves, have only a minimal effect on equipment. However, as the gas cools, a powder of these three components settles on the equipment. Fine powders of the first two components, sodium monoxide and sodium peroxide, have only a minor deleterious effect on equipment. However, the third component, sodium hydroxide, has a major deleterious effect on equipment. Sodium hydroxide, also known as lye, is a highly corrosive material which can corrode contacts or corrode through walls of certain equipment. Studies have also shown that powders of the first two components, sodium monoxide and sodium peroxide, slowly turn into the corrosive third component, sodium hydroxide, when the atmosphere contains substantial moisture. It is also noted that after the powders of the gaseous products are deposited on equipment, some of the powder slowly turns to sodium carbonate ($Na_2CO_3$), although this component is not especially harmful to equipment.

Applicant has considered that, since the harm to equipment occurs primarily by the settling of fine powder of sodium oxide ($Na_2O$), sodium peroxide ($Na_2O_2$) and sodium hydroxide (NaOH), and by the conversion of the first two components into the third, a sodium fire test could be simulated by depositing each of the three components in powder form on the equipment. However, more damage may be done to equipment when the first two components, sodium monoxide and sodium peroxide, turn into sodium hydroxide while lying on the equipment, than when formed as sodium hydroxide prior to depositing it on the equipment. For example, where sodium monoxide lands on plastic (which contains hydrogen molecules), the sodium monoxide ($Na_2O$) may react with hydrogen in the plastic to form sodium hydroxide (NaOH) and thereby corrode the plastic.

In accordance with the present invention, an oxide of sodium, such as sodium monoxide ($Na_2O$) and/or sodium peroxide ($Na_2O_2$) is deposited as a fine powder on equipment to be measured. A level of moisture is established in the same enclosure which contains the equipment, so the deposited oxide of sodium reacts with moisture to form sodium hydroxide on the surface of the equipment, to thereby provide a very conservative test. The equipment is then monitored to determine its operability. Applicant first considered using sodium peroxide, because crystals of this material are widely used in industry and therefore are available for use in testing equipment. However, sodium peroxide becomes highly explosive when ground to a fine powder, if there is a trace of organic material present. The refusual of a commercial grinder of chemicals to grind sodium peroxide to a fine powder for applicant's use, convinced applicant of this. Sodium monoxide is not widely commercially used, but has the important advantage that it is not highly explosive when ground to a fine powder. Since both oxides of sodium form sodium hydroxide in the presence of moisture, applicant prefers to use fine powder of sodium monoxide.

Figure 2:
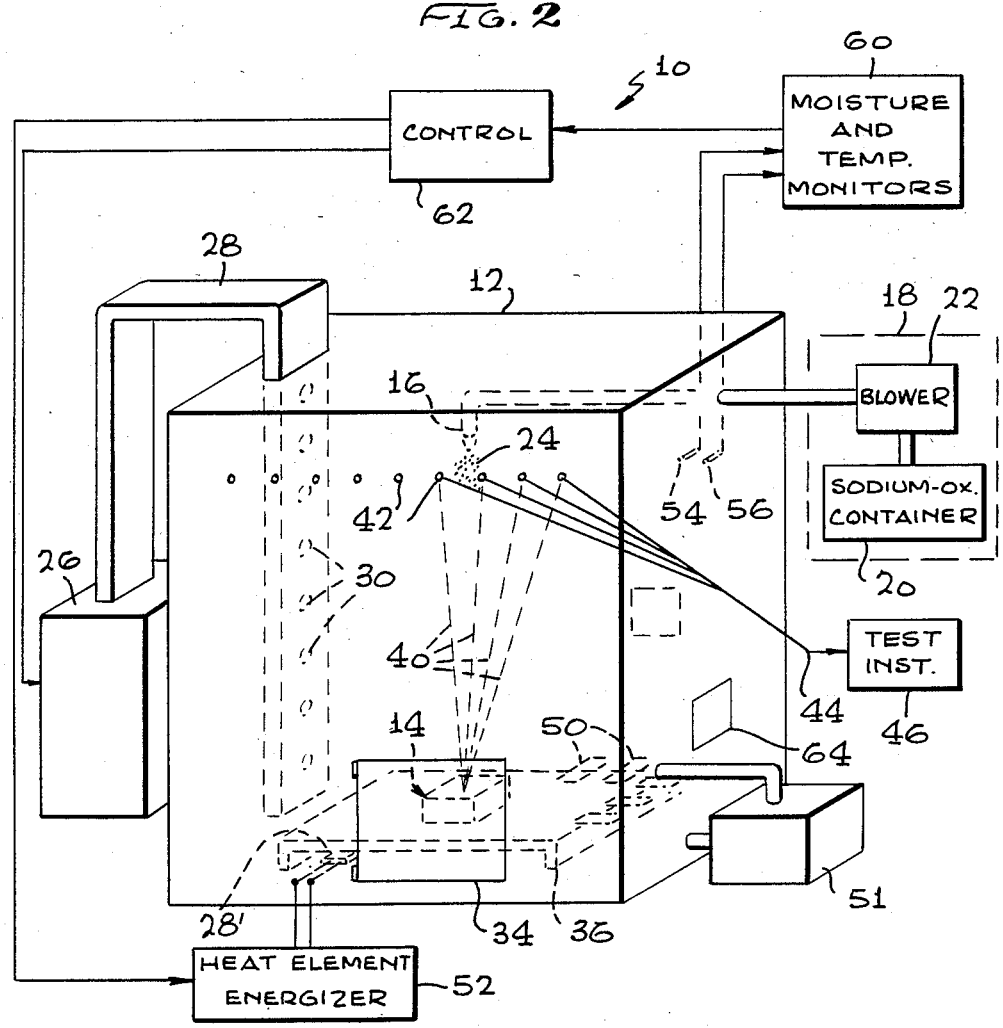
FIG. 2 is a perspective view which indicates a test process conducted in accordance with the present invention.

FIG. 2 illustrates a test setup used by applicant to test equipment for its ability to continue to operate while lying in the immediate vicinity of a sodium fire. The system 10 includes walls 12 forming a chamber in which a piece of equipment 14 such as a relay is placed. A nozzle 16 lies near the top of the walls of enclosure 12, and extends through the enclosure walls to a source 18 of a sodium oxide chosen from the group which includes sodium monoxide ($Na_2O$) and sodium peroxide ($Na_2O_2$), with sodium monoxide ($Na_2O$) being preferred. The source 18 includes a container 20 for the sodium monoxide, and a blower 22 which blows the sodium monoxide powder 24 in the container through the nozzle 16 to fill the enclosure 12 with powder of sodium monoxide.

The sodium monoxide ($Na_2O$) powder is formed so that most of the powder comprises particles of a size between 3 microns and 100 microns. This size range is the size of powder which falls on equipment in an actual sodium fire. After the powder is deposited, steam from a steam generator 26 flows through a duct 28 that extends into the chamber and which has holes 30 for releasing steam into the chamber 12. The steam creates moisture in the chamber. To perform a test representing a situation where a steam pipe has leaked during a sodium fire, a high humidity such as 95% is maintained within the chamber. In most cases a humidity level of at least 20% is maintained in the chamber to represent a low but commonly encountered level of humidity that would be present in an area outside sodium-carrying pipes. In addition, a heating element 28' is provided to maintain a raised temperature to which the environment near a sodium fire would be raised, such as 135° F.

The test can begin by moving the equipment 14 through a chamber opening normally covered by a door 34, and placing the equipment on a stand 36 within the chamber or enclosure 12. Prior to placing the equipment on the stand, several electrical cables 40 are connected between the equipment and terminals 42 that extend through the chamber walls. Additional cables 44 extend from the terminals to a test instrument 46. For a relay, the test instrument can include a source for applying electricity to the terminal contacts, and another source for applying current through the coils of the relay to open and close it. To monitor the amount of sodium monoxide powder deposited, several tabs 50 are placed on the platform within the chamber. The chamber door 34 is then closed.

The container 20 of the sodium monoxide source is filled with the sodium monoxide powder 24. The moisture in the chamber is reduced to a low level which is much below 20%, by use of a dehumidifier 51. Also, a slight vacuum is maintained in the chamber. The blower 22 is operated to pump powder in puffs, to create a cloud of sodium monoxide within the closed chamber 12. At intervals after sodium monoxide powder has been blown into the chamber, a glove box is attached to the side of the chamber at a doorway 64, and one of the tabs 50 is taken out to measure the height of dust that has accumulated thereon. When the height of the dust reaches a predetermined level such as 5 millimeters, representing the amount of dust in a sodium fire for a particular installation, the blowing of dust is stopped.

After the powder settles on the equipment to the required level, the steam generator 26 is started to create a high level of moisture within the chamber. A current source 52 is turned on to begin heating the chamber to a temperature such as 135° F. Moisture and humidity sensors 54, 56 that are connected to a moisture and temperature monitor circuit 60, operate a control circuit 62 that is connected to the steam generator 26 and to the heating element source 52. The equipment is repeatedly tested by the test instrument 46 for an extended period of time such as one month, to determine whether the equipment will continue to function. During the beginning of this extended period, sodium monoxide particles which settle on the equipment will be gradually changed to sodium hydroxide, or lye, and the effect of such corrosive material on the equipment will be measured.

The most damaging component of a sodium fire, sodium hydroxide (NaOH) is applied to the equipment in the most damaging way that occurs in a real sodium fire. This is by forming the sodium hydroxide from an oxide of sodium that builds up on the equipment. If the equipment continues to operate for the required period of time such as one month, when subjected to the most damaging component of a sodium fire, then the equipment is reliably expected to function in the event of a real sodium fire. The test of the present invention, which involves the application of a powder of a sodium oxide such as sodium monoxide ($Na_2O_2$), to the equipment in the presence of moisture, creates conditions very similar to those existing when testing the equipment by creating an actual sodium fire and applying the gaseous products of combustion to the equipment. The present test is similar to such prior art tests, but is somewhat more conservative in that most of the sodium hydroxide is allowed to form directly on the equipment.

The expense of the test of the present invention is a small fraction of that required in the prior art testing which involved the creation of an actual sodium fire. This is largely due to the fact that the gaseous products of a sodium fire, particularly sodium hydroxide, is not generated as a gas and such a gas does not have to be contained over a long period of time. When gaseous products of a sodium fire are present, it may take weeks for powder to settle, the gaseous products settling primarily when moisture causes the aerosol particles to agglomerate. The present powder particles represent primarily the agglomerated settled particles of a sodium fire, and quickly settle onto the equipment.

As discussed above, while sodium monoxide is the preferred powder material, it is also possible to use sodium peroxide, since this also changes to sodium hydroxide in the presence of moisture. However, even though sodium peroxide is easily available at low cost, while sodium monoxide is more difficult to obtain, sodium peroxide has a disadvantage that it is explosive when ground into a fine powder, and will explode if an organic material is present.

In some cooling situations, a cooling medium composed of sodium and potassium, NaK, is used. When potassium is ignited in the presence of air, it also forms the components potassium oxide ($K_2O$), potassium peroxide ($K_2O_2$) and potassium hydroxide (KOH), with the potassium hydroxide being the most corrosive and damaging of the components. The corrosiveness of potassium hydroxide and sodium hydroxide are about the same, so that a test using sodium monoxide or sodium peroxide as described above, also indicates the ability of equipment to function in the presence of potassium or a sodium potassium fire. It is also possible to conduct the test by using powder of a sodium oxide and a potassium oxide, or only of a potassium oxide. Both sodium and potassium are alkalai metals.

Thus, the invention provides a method for testing equipment to determine whether it can continue to function properly in the presence of the products of a sodium fire. The test involves the application of fine powder of a sodium oxide, of sodium monoxide ($Na_2O$) and/or sodium peroxide ($Na_2O_2$), to the equipment in a sealed chamber. The level of moisture in the chamber is also controlled, to a level of at least 20% after the powder is deposited, so the deposited powder turns into sodium hydroxide (NaOH). Such a test costs a fraction of the cost of testing equipment by creating an actual sodium fire.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A method for testing equipment to determine whether it can function when exposed to the gaseous products of combustion of a fire of an alkalai metal, which is chosen from the group which consists of sodium and potassium, in air that contains moisture comprising:
   applying a powder of an oxide of said alkalai metal, with most powder particles of a size between about 3 and 100 microns, to said equipment;
   establishing an ambient atmosphere surrounding said equipment so the atmosphere includes moisture, to turn the metal alkalai oxide into a hydroxide; and
   testing said equipment to determine whether it continues to function after at least some of the alkalai oxide has turned into a hydroxide.

2. The method described in claim 1 wherein:
   said steps of establishing and applying include maintaining a low moisture level of less than 20% in said atmosphere while applying a cloud of said powder to said atmoshpere, and increasing the level of moisture to more than 20% after said powder settles on said equipment.

3. Apparatus for testing electrical equipment to determine whether it will continue to work after exposure to the products of a sodium fire, comprising:
   walls forming an enclosure;
   a source of sodium oxide powder, including a nozzle lying in said enclosure and means coupling said source of powder to said nozzle to apply said powder through said nozzle to said enclosure, so a cloud of powder is created to cause the powder to settle on said electrical equipment;
   means for applying moisture to the environment within said enclosure, for combining of said moisture with powder settled on the equipment to form lye on the equipment;
   an electrical test instrument lying outside said enclosure; and
   an electric conduit extending from said instrument and through the walls of said enclosure to said equipment to enable the testing of said equipment.

4. The apparatus described in claim 3 wherein:
   said source includes a quantity of sodium monoxide powder with most of the powder particles having a diameter between 3 and 100 microns.

5. A method for testing equipment to determine whether it will continue to function when there is a nearby sodium fire, comprising:
   enclosing said equipment in an enclosure;
   loading fine particles of an oxide of sodium into a container, and blowing said particles through a nozzle into said enclosure;
   establishing at least some moisture in said enclosure, whereby to cause the oxide of sodium lying on the equipment to be changed into lye to simulate the most destructive occurance in a potentialy sodium fire; and
   testing said equipment while it lies in said enclosure.

* * * * *